United States Patent [19]

Molin et al.

[11] Patent Number: 5,190,755
[45] Date of Patent: Mar. 2, 1993

[54] NUTRIENT COMPOSITION AND METHOD FOR THE PREPARATION THEREOF

[75] Inventors: Nils Molin, Lund; Carl-Erik Albertsson, Saltsjö-Duvnäs; Stig Bengmark, Lund; Kåre Larsson, Bjärred, all of Sweden

[73] Assignee: Probi AB, Lund, Sweden

[21] Appl. No.: 571,635

[22] PCT Filed: Mar. 9, 1989

[86] PCT No.: PCT/SE89/00114

§ 371 Date: Nov. 9, 1990

§ 102(e) Date: Nov. 9, 1990

[87] PCT Pub. No.: WO89/08405

PCT Pub. Date: Sep. 21, 1989

[30] Foreign Application Priority Data

Mar. 9, 1988 [SE] Sweden ............................. 880022-2

[51] Int. Cl.$^5$ .................... A01K 63/00; A61K 37/00; C12N 9/42; A21D 2/00
[52] U.S. Cl. .................................. 424/93 J; 426/18; 426/20; 426/21; 435/209
[58] Field of Search .................... 426/18, 19, 20, 21, 426/52; 424/93

[56] References Cited

U.S. PATENT DOCUMENTS

| | | | |
|---|---|---|---|
| 2,194,672 | 3/1940 | Porter | 426/18 |
| 2,452,534 | 11/1948 | Jeffreys | 426/18 |
| 4,056,637 | 11/1977 | Hagiwara | 426/52 |

Primary Examiner—Douglas W. Robinson
Assistant Examiner—Jane A. Williams
Attorney, Agent, or Firm—Oblon, Spivak, McClelland, Maier & Neustadt

[57] ABSTRACT

A nutrient composition for administration to patients in, for example, feeding by tube, or for use as a health drink is described. The nutrient composition comprises a fermented cereal-based product, enzyme and, optionally, further nutrient components, in combination with lactobacilli. Also described is a method of preparing a nutrient composition for administration to patients, inter alia in feeding by tube, or for use as a health drink, in which method a cereal flour is mixed with water, a-amylase and, optionally, a protease, the mixture is brought to the boil under agitation, allowed to cool and mixed with B-glucanase which is allowed to act until the viscosity of the mixture has decreased to below 0.020 Pas, whereupon the mixture is fermented.

10 Claims, No Drawings

NUTRIENT COMPOSITION AND METHOD FOR THE PREPARATION THEREOF

The present invention relates to a nutrient composition for administration to patients, inter alia for feeding by tube, and for use as a health drink, or as a nutrient for horses, as well as to a method for the preparation of such a nutrient composition.

One medical problem in major operations of the abdomen is the general collapse of the organs due to infections from the large intestine. One way of reducing the risks of infections is to feed the patient by tube, thereby to keep the intestine working. This method imposes special demands on the tube-administered nutrient. Not only must the nutrient be nutrimentally complete; it must also be so thin-bodied that it can be administered via a thin plastics catheter, without necessitating a daily supply of more than 2-3 liters of liquid.

Furthermore, it is a great advantage if the nutrient can affect the composition of the patient's intestinal flora which frequently is disturbed in newly operated patients, and this may sometimes result in symptoms of poisoning. This applies especially to patients who have been or are being treated with antibiotics.

A further field of application where there is a need for specific nutrients is horse-racing. Horses, under stress, for example in connection with a race, frequently contract diarrhoea, which may affect their performance.

Present-day nutrient compositions used for feeding by tube substantially consist of fractionated food components recombined according to the recommendations of dieticians. The known nutrient compositions suffer from a number of shortcomings. If they have a suitable low viscosity for administration through narrow tubes, their concentration of the requisite nutrients will instead be too low, and therefore very large amounts must be given. Furthermore, the known nutrient compositions have a disagreeable taste and do not affect the patient's intestinal flora.

Indicia showing that certain intestine-specific lactobacilli have a special ability to counteract the establishment of undesired microorganisms in the intestine, have been reported by, for example, Wallström et al, 1987, J. Appl. Bacteriol. 62:513-520; Sherwood et al, 1987, Lancet, Dec. 26, 1519.

It is an object of the present invention to provide a nutrient composition for administration to patients, inter alia in feeding by tube, or for use as a health drink, said composition having a viscosity which is suitable for administration by tube, which is tasty, and which, furthermore, contains lactobacilli suitable for the intestine.

The nutrient composition according to the invention, especially when it contains fermented oats, is also highly suitable for administration to horses before a race for the prevention of diarrhoea.

A further object of the invention is to provide a method of preparing a nutrient composition for administration to patients, inter alia for feeding by tube, or for use as a health drink.

The nutrient composition according to the invention comprises a fermented cereal-based product, enzymes and, optionally, further nutrient components, in combination with lactobacilli.

The method according to the invention is characterised in that cereal flour is mixed with water and α-amylase, and that the mixture is brought to the boil under agitation, allowed to cool and mixed with β-glucanase which is allowed to act until the viscosity of the mixture has decreased to below 0.020 Pas, whereupon the mixture is fermented.

A patient who is fed by tube can be supplied with the suitable lactobacilli in basically three different ways, viz. (i) the desired lactobacillus can be utilised for fermenting the product; (ii) a lactobacillus culture can be added separately to the fermented product; and (iii) the lactobacillus culture and the rest of the nutrient composition can be administered separately.

The lactobacillus desired in the final product is preferably used already for fermenting the product, whereby there is conveniently obtained a fermented product containing the desired culture, without necessitating the addition of further bacteria cultures.

The lactobacilli supplied not only have a favourable effect on the patient's intestinal flora; they also contribute to reducing the viscocity of the nutrient composition during the fermentation process. Proteins are degraded to short dextrins and amino acids. β-Glucanes are degraded by the enzyme β-glucanase. The result is a readily digested product which is rich in flavour and has adequate shelf life.

In the preferred embodiment, the fermenting ability of the lactobacilli is utilised, and at the same time the patient's need of viable lactobacilli is satisfied.

The lactobacillus cultures selected are special cultures which in vitro have certain characteristics significant to the contemplated use. Suitable cultures are obtained by extracting and isolating lactobacilli that have established themselves in the intestine of healthy persons. The following characteristics are taken into account in selecting a suitable production strain:
the ability to ferment oat-flour
the specific growth rate
the ability to rapidly reduce pH during the fermentation process
suitable final pH upon fermentation
the acid fermentation pattern from glucose
survival upon freeze-drying
resistance to bile
resistance to antibiotics
plasmide contents
the ability to spontaneously adhere to the intestine
reuterine production in the presence of glycerol
cholesterol interaction
the ability to produce desirable flavouring agents
the ability to degrade β-glucanes All of these characteristics need not occur in one and the same culture, but it is recommended to choose a culture that has as many as possible of these characteristics.

A preferred culture is an isolate of intestine-specific Lactobacillus reuteri and a preparation of lipase enzymes stimulating the production of antimicrobial substances (reuterine) by said lactobacillus. Other useful organisms are, for example, *Lactobacillus fermentum, L. acidofilus, L. alimentarius, L. brevis sp. lindneri, L. plantarum, L. leuconostoc* and *L. dextranicum.*

The basis of the nutrient composition is cereal flour. It has surprisingly been found that especially a suspension of oat-flour in water is an ideal basis for lactic acid fermentation. Of all cereals, oat has the best amino acid balance, and the lipid fraction contains the maximum amount of polar lipids. It has been shown, by works in progress, that this lipid type has a favourable effect on the gastric mucosa.

In countries in which there is a shortage of oats, also other cereals, such as corn, may however be used.

In order to obtain a nutrient composition which is as complete as possible, the composition can be mixed with soya flour before fermentation to supplement the protein and fat contents.

Furthermore, minerals and vitamin contents may be supplemented before or after fermentation.

In the method, the cereal flour is suspended in water, and α-amylase is added, either in the form of malt flour, pure α-amylase, or in the form of α-amylase-containing microorganisms. The suspension is brought to the boil under agitation to the suitable temperature which, if it is an oat suspension, is maximally 95° C. Then, the suspension is allowed to cool about 50° C., whereupon β-glucanase is added which is allowed to act for 1-2 hours at about 50° C., whereupon the viscosity has decreased to about 0.020 Pas.

The cereal flour can also be treated with various proteases in order to degrade the proteins therein.

It is recommended that the product be then enriched with soya flour.

Finally, the mixture is mixed with a suitable bacteria culture, preferably the lactobacillus culture that is to be present in the final composition, and fermented at a temperature that should lie between 30° and 40° C.

The composition according to the invention may be used either as it is, in the form of an aqueous solution, or the aqueous solution can be concentrated and diluted immediately before use. Such a solution has an estimated shelf life of about 8 days at cooling temperature.

Alternatively, the nutrient solution can be freeze-dried and then dissolved in water before use. An additionally improved shelf life is obtained if the cereal flour, preferably the oat-flour is defatted before use by extraction in a solvent, such as ethanol or supercritical carbon dioxide, whereupon the resulting oil, after emulsifying and spray-drying is recycled to the product after freeze-drying.

The method described above thus gives a fermented nutrient composition which is optimal for enteral nutrition and which contains physiologically active cells of a specially selected lactobacillus culture in high concentration. Furthermore, the product gives a rapid colonisation in the small intestine.

The preferred freeze-drying imparts to the nutrient composition a much increased resistance to fat oxidation, whereby a satisfactory shelf life is obtained.

In two instances, the solution was administered to patients under intensive care for nutritional disorders and sepsis due to colonisation of aerobic intestinal bacteria. When the treatment began, both patients were apathetic because no previous treatment had proved successful. After administration of the nutrient solution according to the invention, containing lactobacilli, by tube to the intestine, both patients made a dramatic recovery.

The nutrient preparation according to the invention can be used also as a supplementary nourishment in general, for example in the form of a health drink.

The invention will now be described in more detail with reference to the following nonrestrictive Example

EXAMPLE 34 g oat-flour (Mp oat-flour, product name) are suspended in 100 g water together with 3.4 g malt flour alternatively 1 g pure α-amylase. The oat-flour suspension is brought to the boil under agitation to 95° C., whereupon it is allowed to cool to about 50° C. Then, 1% β-glucanase (calculated on the amount of oat-flour) is added and allowed to act for 1-2 hours at 50° C., whereby the viscosity is decreased to about 0.020 Pas.

After that, the suspension is enriched with soya flour.

Finally, a lactobacillus culture is added, selected with due regard to the characteristics mentioned in the general part of the specification, whereupon the suspension is fermented at, for example, 37° C. for 20 hours.

To further enrich the product, further fat, sodium, vitamin A, vitamin D, riboflavin, vitamin $B_6$, folic acid and ascorbic acid and, optionally, also potassium and calcium are added.

The product prepared in this manner has the energy and nutrient contents stated in Table 1.

TABLE 1

| | | | ENRICHMENT/100 ml | |
|---|---|---|---|---|
| | Recommended contents/100 ml | Oat suspension/100 | Alt. 1 Skim milk powder 3.7 g | Alt. 2 Soya flour 2.8 g |
| Energy KJ | 424 | 424* | 475* | 513* |
| Protein g | 4.7 | 3.4 | 4.7* | 4.7* |
| Fat g | 3.5 | 1.8 | 1.8 | 1.82 |
| Carbohydr. g | 11.8 | 16.6* | 18.5* | 17.6* |
| Ca mg | >51 | 13.5 | 58.9* | 20.8 |
| Fe mg | >0.94 | 1.32* | 2.46* | 1.62* |
| P mg | 70 | 98* | 133* | 116* |
| Mg mg | >28 g | 35* | 40* | 44* |
| Na mg | 80 | 1.25 | 21 | 1.28 |
| K mg | 148 | 84 | 150* | 134 |
| ret. eqv. mg | >0.05 | — | 0.011 | 0.0001 |
| vit. D μg | >0.28 | — | traces | — |
| Thiamine mg | >0.070 | 0.15* | 0.19* | 0.18* |
| Ribofl. mg | >0.094 | 0.037 | 0.11* | 0.04 |
| vit. $B_6$ mg | >0.11 | 0.04 | 0.053 | 0.059 |
| Folic acid μg | 40 | 0.006 | 0.006 | 0.06 |
| Ascorb. mg | >3.3 | — | 0.3 | — |

*Satisfies demands for recommended amount of nutrition

We claim:

1. A method for preparing a nutrient composition for enteral nutrition, comprising:
   admixing an oat-flour, water and α-amylase to form a first admixture;
   heating said first admixture to a temperature not higher than 95° C., under agitation to form a stable suspension;
   cooling said first admixture to about 50° C.;
   adding a β-glucanase to said cooled first admixture to form the second admixture;
   holding said second admixture at about 50° C. until the viscosity of said second admixture is less than 0.020 Pas;
   adding lactobacilli, having the ability to spontaneously adhere to the intestine, to said second admixture of reduced viscosity to form the third admixture; and
   fermenting said third admixture at between 30° C. and 40° C. to form the nutritional composition.

2. The method according to claim 1, wherein said first admixture further comprises a protease.

3. The method according to claim 1, further comprising adding soya flour to said third admixture prior to fermenting said third admixture.

4. The method according to claim 1, wherein said lactobacilli is isolated from the intestine of a healthy human being.

5. The method according to claim 1, wherein said lactobacilli is *L. reuteri, L. fermentum, L. acidofilus, L.*

*alimentarius, L. brevis sp. lindneri, L. plantarum, L. leuconostoc* or *L. dextranicum*.

6. The method according to claim 1, further comprising adding mineral and vitamins to said nutrient composition, said addition being affected before or after fermentation of said third admixture.

7. The method according to claim 1, further comprising the steps of freeze-drying said fermented nutrient composition for storage; and redissolving said freeze-dried material in water prior to use.

8. The method according to claim 7, further comprising the steps of defatting said oat-flour, prior to said admixture with water and amylase, to obtain a recovered fat; and admixing said recovered fat with said freeze-dried material.

9. The nutrient composition produced according to the method of claim 7.

10. The nutrient composition produced according to claim 9, wherein the energy content of said nutrient composition is at least 424 kJ/100 ml.

* * * * *

UNITED STATES PATENT AND TRADEMARK OFFICE
CERTIFICATE OF CORRECTION

PATENT NO. : 5,190,755

DATED : March 2, 1993

INVENTOR(S) : Nils Molin et al.

It is certified that error appears in the above-identified patent and that said Letters Patent is hereby corrected as shown below:

On the title page, Item [30],

The Foreign Application Priority Data is incorrect, should read:

--Mar. 9, 1988 [SE] Sweden.................8800822-2--

Signed and Sealed this

Twenty-fifth Day of January, 1994

*Attest:*

BRUCE LEHMAN

*Attesting Officer*     Commissioner of Patents and Trademarks